United States Patent [19]

Yamada et al.

[11] Patent Number: 4,833,082
[45] Date of Patent: May 23, 1989

[54] NEW RESTRICTION ENZYME AND PROCESS FOR PRODUCING THE SAME

[75] Inventors: Yuzo Yamada, Fujieda; Makoto Murakami, Shizuoka, both of Japan

[73] Assignee: Takara Shuzo Co., Ltd., Kyoto, Japan

[21] Appl. No.: 905,455

[22] Filed: Sep. 10, 1986

[30] Foreign Application Priority Data

Dec. 12, 1985 [JP] Japan .................................. 60-279886

[51] Int. Cl.⁴ .......................... C12N 9/22; C12P 19/34; C12R 1/02
[52] U.S. Cl. ..................................... 435/199; 435/91; 435/823
[58] Field of Search .......................... 435/91, 199, 823; 536/27

[56] References Cited

PUBLICATIONS

Yamada, Y., et al. (1985) Agric. Biol. Chem., 49(12) 3627–3629.
Degtyarev. S. Kh. et al. (1987) Chemical Abstracts, 106:209994d.
Roberts, R. J. (1987) Nucleic Acids Research, 15 (suppl.) r189, r190, r215.

Primary Examiner—Thomas G. Wiseman
Assistant Examiner—Charles L. Patterson
Attorney, Agent, or Firm—Wenderoth, Lind & Ponack

[57] ABSTRACT

A restriction enzyme, ApaLI, which recognizes the base sequence in a double-stranded deoxyribonucleic acid molecule as shown below, and cleaves it at the arrow-marked sites,

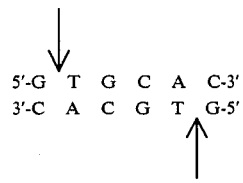

wherein A, G, T and C represent adenosine, guanosine, thymidine and cytidine, respectively. Also provided is a process for producing this enzyme, by growing a microorganism belonging to the genus *Acetobacter*.

3 Claims, No Drawings

NEW RESTRICTION ENZYME AND PROCESS FOR PRODUCING THE SAME

This invention relates to a new restriction enzyme and to a process for producing the same. More particularly, it relates to a new restriction enzyme, ApaLI, produced by a bacterium belonging to the genus Acetobacter, and to a process for producing the same.

Restriction enzymes are endonucleases that are capable of recognizing a specific sequence of bases on a deoxyribonucleic acid (DNA) molecule and of cleaving the double-stranded DNA chain at specific sites. As a result of recent progress in molecular genetics, biochemistry and related sciences, it is now clear that DNA is the carrier of genetic information, and restriction endonucleases have been extensively used for various purposes, e.g. clarification of genetic diseases, mass production of genetic materials based on genetic engineering, etc. About 100 kinds of endonucleases have so far been isolated from many microorganisms, each being identified by the specific base sequence it recognizes and by the cleavage pattern it exhibits.

A large number of restriction enzymes with diversified enzymatic characteristics are necessary for successful gene manipulation. To the best of our knowledge, however, no restriction enzyme yet discovered is capable of recognizing the base sequence in a double-stranded DNA molecule as shown below and of cleaving it at the arrow-marked sites,

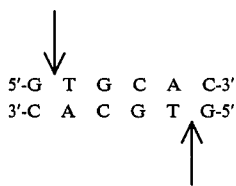

(wherein A, G, T and C represent adenosine, guanosine, thymidine and cytidine, respectively).

Therefore, the object of the present invention is to provide a novel restriction enzyme which is capable of recognizing the base sequence in the double-stranded deoxyribonucleic acid mentioned above and of cleaving the same at the above indicated arrow-marked sites.

One aspect of this invention relates to restriction enzyme, ApaLI, having the following properties:

(a) Action and Substrate Specificity: Recognizes the base sequence in a double-standard DNA molecule as shown below, and cleaves it at the arrow-marked sites,

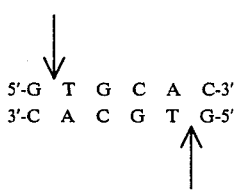

(wherein A, G, T and C represent adenosine, guanosine, thymidine and cytidine, respectively).
(b) Optimal pH range: 7.5 to 8.5
(c) Stable pH range: 7.0 to 9.0
(d) Optimal temperature: Approximately 37° C.
(e) Molecular weight: 26,000±8,000 (gel filtration method)

Restriction enzyme ApaLI of this invention cleaves double-stranded λ-DNA at four sites, φX174 RF at one site, and pBR322 at three sites.

Another aspect of this invention relates to a process for producing restriction enzyme, ApaLI, which comprises growing a microorganism belonging to the genus Acetobacter and capable of producing ApaLI in a culture medium and collecting the enzyme thus formed from the culture product.

The present inventors have been working on taxonomy, physiology, biochemistry and genetics of acetic acid bacteria. During the course of these studies, we have discovered a new Type-II restriction enzyme (designated as ApaLI) from a bacterium belonging to the genus Acetobacter. This invention was accomplished based on these findings.

Thus the object of this invention is to provide a process for producing a restriction enzyme which comprises growing a microorganism belonging to the genus Acetobacter and collecting a new Type-II restriction enzyme ApaLI from the microbial cells.

Any strain of Acetobacter capable of producing ApaLI can be used for the purpose of this invention; a typical example is Acetobacter pasteurianus IFO 13753, which is stored in the Institute for Fermentation, Osaka (IFO). This strain has been deposited in the Fermentation Research Institute (under the Agency of Industrial Science and Technology) as FERM BP-877.

Any nutrients that can be assimilated by ApaLI-producing strains may be added to the culture medium. Glucose, sucrose, maltose, lactose, glycerol, ethanol, lactates, various fats and oils, and others may be used as carbon source, while yeast extract, peptone, defatted soybeans, corn steep liquor, bouillon and others are suitable as nitrogen source. Minerals and metal salts, e.g. phosphates, potassium salts and magnesium salts, as well as vitamins and growth promoting substances, may also be added as required.

The yield of ApaLI varies greatly depending on culture conditions. Best results are generally obtained at a temperature in the range from 20° to 35° C. and at a pH in the range from 3 to 8; the highest output is achieved in one to three days by culture with aeration and agitation. It is needless to say that optimal culture conditions should be selected case by case according to the strain used and the composition of the culture medium. ApaLI produced by the process of this invention is accumulated inside the microbial cells.

The microbial cells containing ApaLi can be separated from the culture liquid, for example, by centrifugation.

This enzyme can be extracted and purified by using known techniques commonly employed for restriction endonucleases. The collected microbial cells are dispersed in a suitable buffer, and then broken down by ultrasonic treatment to allow extraction of the enzyme by the buffer solution. After removal of the residue by ultracentrifugation, ammonium sulfate is added to the supernatant for salting out, and the precipitate which separates out is dissolved in a potassium phosphate buffer (pH: 7.5) and dialyzed against a buffer of the same composition. The dialyzate is purified by ion-exchange chromatography, molecular-sieve chromatography and affinity chromatography, giving the restriction enzyme of this invention. In an example, the dialyzate is adsorbed in DEAE-cellulose DE52 (Wattman)

packed in a column, followed by elution with 0 to 1.0M potassium chloride solutions. The active fractions collected are then absorbed on Affigel blue agarose (Bio-rad Laboratories), followed by elution with 0 to 1.0M potassium chloride solutions. The active fractions were further purified by adsorption on heparin-Sepharose CL-6B (Pharmacia Fine Chemicals) and elution with 0 to 1.0M potassium chloride solutions, affording a standard sample of ApaLI.

The activity of this enzyme was determined according to the method described below.

A substrate solution of the composition shown in Table 1 was prepared.

TABLE 1

| 10 mM | Tris-HCl, pH: 7.5 |
|---|---|
| 7 mM | MgCl$_2$ |
| 7 mM | 2-Mercaptoethanol |
| 50 mM | NaCl |
| 0.01% | Bovine serum albumin |
| 1.0 µl | λ-DNA |

This substrate solution (50 µl) was preheated to 37° C., the sample of ApaLI to be tested was added to allow the enzymatic reaction to proceed at that temperature, and the reaction was stopped 10 minutes later by addition of 5 µl of a terminator solution (1% SDS, 50% glycerol, 0.02% Bromophenol Blue). The reaction mixture was applied to a 1% agarose slab gel, and electrophoresis was conducted at a constant voltage of 10 v/cm for one to two hours. The buffer solution used was 90 mM Tris-borate buffer containing 2.5 mM EDTA (pH: 8.3), for the electrophoresis.

DNA bands can be detected by UV irradiation if 0.5 µg/ml ethidium bromide is previously added to the gel. Electrophoresis was regarded as complete when the number and intensity of the bands for DNA fragments no longer changed.

The enzyme activity which ensures complete decomposition of 1 µg λ-DNA after one hour's reaction at 37° C. was defined as one unit.

The restriction enzyme ApaLI obtained by the process of this invention has the properties as described below.

(1) Action and substrate specificity

This enzyme is capable of recognizing the base sequence on a double stranded DNA molecule as shown below and cleaving it at the arrow-marked sites,

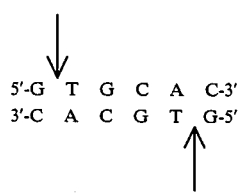

The recognition base sequence of this enzyme ApaLI was determined as described below.

ApaLI cleaved φX174 RF DNA at one site and pBR 322 DNA at three sites, but failed to cleave SV40 DNA. This indicates that ApaLI recognizes and cleaves either 5'-GTGCAC-3' or 5'-TPyCGPuA-3' on a DNA molecule (wherein Py represents thymidine or cytidine, and Pu expresses adenosine or guanosine). In a double digestion test of φX174 RF DNA using ApaLI and BbeI, the former cleaved nearly at the middle of the longer fragment (3429 bp) of BeI digests. The resultant two fragments were both smaller than the smaller fragment (1957 bp) of BbeI digests of φX174 RF DNA. It was clear from these experimental data that ApaLI cleaved φX174 RF DNA at a site between coordinates 4483 and 4933. Sequence 5'-GTGCAC-3' actually exists in φX174 RF DNA at a site between coordinates 4779 and 4784, and this fact is in agreement with the experimental data obtained above.

On pBR322 DNA, the same palindromic sequence as above was found at three sites (coordinates 2291, 2789 and 4035). ApaLI cleaved this DNA at these three sites, giving three fragments (498 bp, 1246 bp and 2619 bp, respectively). Upon treatment of these three fragments with HindIII, only the largest fragment (2619 bp) was cleaved to afford two minor fragments, 357 bp and 2262 bp, with the other two small fragments (498 bp, 1246 bp) being left uncleaved. This also shows that ApaLI is capable of recognizing and cleaving the sequence

5'-GTGCAC-3' in pBR322 DNA, as in the case with φX174 RF DNA. It was also proved from the above result that the other possible sequence 5'-TPyCGPuA-3' is not recognized by ApaLI.

The sites of cleavage by the restriction enzyme of this invention, ApaLI, were determined as described below.

φX174 RF DNA was digested with ApaLI and phosphorylated at the 3'-terminal end with 2',3'-dideoxyadenosine-5'-[α-$^{32}$P]triphosphate and terminal transferase. The $^{32}$P-labeled molecule thus obtained was then digested with XmnI, giving two labeled DNA fragments, 338 bp and 636 bp, which were sequenced by the method of Maxam and Gilbert. It became clear that the fragment of 338 bp has a sequence 3'-GAAATACGC at the 3'terminal end, and the fragment of 636 bp has a sequence of 3'-GGCGTACCT at the 3' terminal. This result can be interpreted in terms of the base sequence of φX174 RF DNA as shown below, indicating that φX174 RF DNA has been cleaved at the arrow-marked sites,

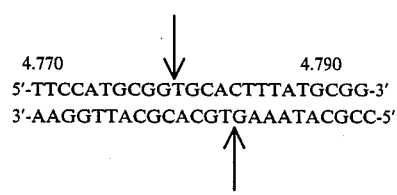

It was thus concluded that this enzyme is capable of recognizing the base sequence as shown below and cleaving it at the arrow-marked sites,

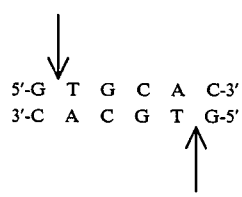

(2) Optimal conditions for enzymatic activity
(a) Optimal temperature
The optimal temperature for ApaLI was approximately 37° C.

(b) Optimal pH

The optimal pH of ApaLI was in the range from 7.5 to 8.5.

(c) Salt concentration

The optimal salt concentration of ApaLI was in the range from 40 to 50 mM, the relative activity being 75% for 0 mM and 50% for 100 mM NaCl.

(d) Stable pH range

Stable pH range of ApaLI was 7.0 to 9.0.

The following Example will further illustrate this invention but is not intended to limit its scope.

EXAMPLE

*Acetobacter pasteurianus* IFO 13753 was cultured in 160 liters of a medium having the composition shown in Table 2 at 26° C. for 19 hours with aeration and agitation, and the grown cells (about 280 g on wet basis) were collected from the culture broth (160 l) by means of a refrigerated centrifuge.

TABLE 2

| Polypeptone | 5 g |
|---|---|
| Yeast extract | 5 g |
| Glucose | 5 g |
| Glycerol | 15 g |
| Deionized water | 1 l |
| pH | 6.8 |

One hundred grams of the bacterial cells obtained above were suspended in 200 ml of an extractive buffer solution (50 mM Tris-HCl, 10 mM 2-mercaptoethanol, 1 mM EDTA; pH: 7.5), the suspension was treated in an ultrasonic crusher to break down the cell walls, and the resulting mixture was centrifuged (100,000×g, one hour) to remove the residue.

To the extract thus obtained, was added a 20% aqueous solution of streptomycin sulfate to give a final concentration of 2%. The mixture was stirred for 30 minutes and centrifuged, giving a supernatant free of nucleic acid. Ammonium sulfate was added to this supernatant to 70% saturation, the precipitate which separated out was collected by centrifugation and dissolved in buffer solution A (10 mM potassium phosphate buffer containing 10 mM 2-mercaptoethanol, 1 mM EDTA and 5% glycerol; pH: 7.5), and the solution was dialyzed overnight against buffer solution A.

The dialyzate was then adsorbed on DEAE-cellulose DE52 packed in a 35×100 mm column and previously equilibrated with buffer solution A. After washing with buffer solution A, the adsorbed portion was eluted with 0 to 1.0M potassium chloride solutions (linear concentration gradient technique). ApaLI activity was detected in fractions corresponding to 0.18 to 0.38M KCl concentration.

Then these fractions were collected and dialized overnight against the buffer solution A, and the dialyzate was adsorbed on a column (24×110 mm) of Affigel blue agarose (Bio-rad Laboratories; 100–200 mesh) previously equilibrated with the buffer solution A. Then the column was washed with the buffer solution A and eluted with the buffer solutions A having a linear concentration gradient of 0–1.0M potassium chloride. ApaLI activity was detected in the fraction corresponding to 0.14–0.32M KCal.

These active fractions were collected and dialyzed overnight against buffer solution A, the dialyzate was adsorbed on heparine-Sepharose CL-6B packed in a 15×60 mm column and previously equilibrated with buffer solution A, and the adsorbed portion was eluted with 0 to 1.0M potassium chloride solutions (linear concentration gradient technique). ApaLI activity was detected in fractions corresponding to 0.13 to 0.34KCl concentration. The active fractions were collected and dialyzed against buffer solution A containing 50% glycerol until the volume became halved, affording the final standard sample of ApaLI.

This standard sample was free from any nonspecific DN-ase or phosphatase.

The purification method described above gave 39,000 units of ApaLI from 100 g of wet microbial cells; the relative activity was enhanced by a factor of 50 with a yield of 2%.

As may be apparent from the foregoing, this invention provides a novel restriction enzyme, ApaLI, having unique substrate specificity that has never been known, and a process for producing the same on an industrial basis.

What is claimed is:

1. Restriction enzyme, ApaLI, having the following properties:
    (a) Action and substrate specificity: Recognizes the base sequence in a double-stranded deoxyribonucleic acid molecule as shown below, and cleaves it at the arrow-marked sites,

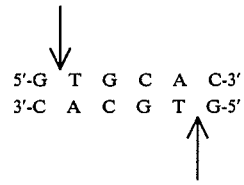

wherein A, G, T and C represent adenosine, guanosine, thymidine and cytidine, respectively
    (b) Optimal pH range: 7.5 to 8.5
    (c) Stable pH range: 7.0 to 9.0
    (d) Optimal temperature: Approximately 37° C.
    (e) Molecular weight: 26,000±8,000 by gel filtration method.

2. A process for producing restriction enzyme, ApaLI, which comprises growing a microorganism belonging to the genus *Acetobacter* and capable of producing ApaLI in a culture medium and collecting the enzyme thus formed from the culture broth.

3. The process as defined in claim 2, wherein said microorganism is *Acetobacter pasteurianus* IFO 13753.

* * * * *